United States Patent
Harigae

(10) Patent No.: US 9,156,252 B2
(45) Date of Patent: Oct. 13, 2015

(54) LIQUID EJECTION APPARATUS AND SENSOR UNIT

(71) Applicant: CANON KABUSHIKI KAISHA, Tokyo (JP)

(72) Inventor: Ryo Harigae, Koganei (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/564,350

(22) Filed: Dec. 9, 2014

(65) Prior Publication Data

US 2015/0174894 A1 Jun. 25, 2015

(30) Foreign Application Priority Data

Dec. 20, 2013 (JP) .................................. 2013-263665

(51) Int. Cl.
| | |
|---|---|
| *B41J 2/01* | (2006.01) |
| *B41J 2/045* | (2006.01) |
| *G01D 11/24* | (2006.01) |
| *G01N 21/01* | (2006.01) |
| *B41J 2/215* | (2006.01) |

(52) U.S. Cl.
CPC .............. *B41J 2/0456* (2013.01); *G01D 11/245* (2013.01); *G01N 21/01* (2013.01); *B41J 2/215* (2013.01); *G01N 2201/022* (2013.01)

(58) Field of Classification Search
CPC ........ B41J 2/04573; B41J 2/515; B41J 3/543; B41J 2/2146; B41J 29/393; B41J 2/04505; B41J 2/2132; B41J 2/2135

USPC ................................ 347/9–12, 14, 19, 40–43
See application file for complete search history.

(56) References Cited

U.S. PATENT DOCUMENTS

| | | | | |
|---|---|---|---|---|
| 5,534,895 | A | * | 7/1996 | Lindenfelser et al. .......... 347/19 |
| 2009/0213167 | A1 | | 8/2009 | Motooka et al. |

FOREIGN PATENT DOCUMENTS

| | | |
|---|---|---|
| JP | 2005-186422 A | 7/2005 |
| JP | 2007-062222 A | 3/2007 |
| JP | 2009-196253 A | 9/2009 |
| JP | 2009-285870 A | 12/2009 |
| JP | 2013-202827 A | 10/2013 |
| JP | 2013-212679 A | 10/2013 |

OTHER PUBLICATIONS

Office Action in Japanese Patent Application No. 2013-263665, dated Jul. 28, 2015.

* cited by examiner

*Primary Examiner* — Thinh Nguyen

(74) *Attorney, Agent, or Firm* — Fitzpatrick, Cella, Harper & Scinto

(57) ABSTRACT

A liquid ejection apparatus and a sensor unit are capable of reducing the amount of mist adhering to an optical element. The liquid ejection apparatus includes a carriage including an ejection head mounted thereon for ejecting a liquid, and a sensor unit accommodating an optical element attached to the carriage, wherein the sensor unit has a first opening and a second opening which is communicated with the first opening and forms a light path between the optical element and the medium.

11 Claims, 13 Drawing Sheets

LIQUID EJECTION APPARATUS AND SENSOR UNIT

BACKGROUND OF THE INVENTION

1. Field of the Invention

The present invention relates to a liquid ejection apparatus and a sensor unit.

2. Description of the Related Art

In a liquid ejection apparatus which applies a liquid to a medium by ejecting the liquid from an ejection port of a liquid ejection head and conveying the medium while moving a carriage carrying the liquid ejection head, the structure has been known in which a sensor is attached as a sensor unit to the carriage.

Japanese Patent Laid-Open No. 2007-62222 discloses the structure in which an optical element (sensor) composed of a light emitting element and a light receiving element is attached to a carriage so that light emitted from the light emitting element to a medium and reflected by the medium is received at the light receiving element.

When ink droplets are ejected from the ejection port of the liquid ejection head, mist may be generated along with ink droplets applied to the medium. Adhesion of mist to the light emitting element or the light receiving element may induce change in the amount of light emitted from the light emitting element, and change in the amount of light received at the light receiving element, thereby deteriorating detection accuracy of the sensor.

SUMMARY OF THE INVENTION

The present invention provides liquid ejection apparatus and a sensor unit capable of reducing the amount of mist adhering to an optical element.

According to a first aspect of the present invention, there is provided a liquid ejection apparatus, including: a carriage including an ejection head mounted thereon for ejecting a liquid and moving, and a sensor unit accommodating an optical element attached to the carriage, wherein the sensor unit has a first opening and a second opening which is communicated with the first opening and forming a light path between the optical element and the medium.

According to a second aspect of the present invention, there is provided a sensor unit, including: an optical element, and a housing accommodating the optical element, wherein the housing has a light path opening forming a light path between the optical element and the outside, and a ventilation opening opened in the direction intersecting with the opening direction of the light path opening and communicated with the light path opening.

According to the structure described above, when an ejection head ejects a liquid and mist is generated, it is possible to reduce the amount of mist adhering to an optical element.

Further features of the present invention will become apparent from the following description of exemplary embodiments (with reference to the attached drawings).

DESCRIPTION OF THE EMBODIMENTS

Hereinafter, an exemplary embodiment according to the present invention will be in detail described with reference to the accompanying drawings.

Figure 1:
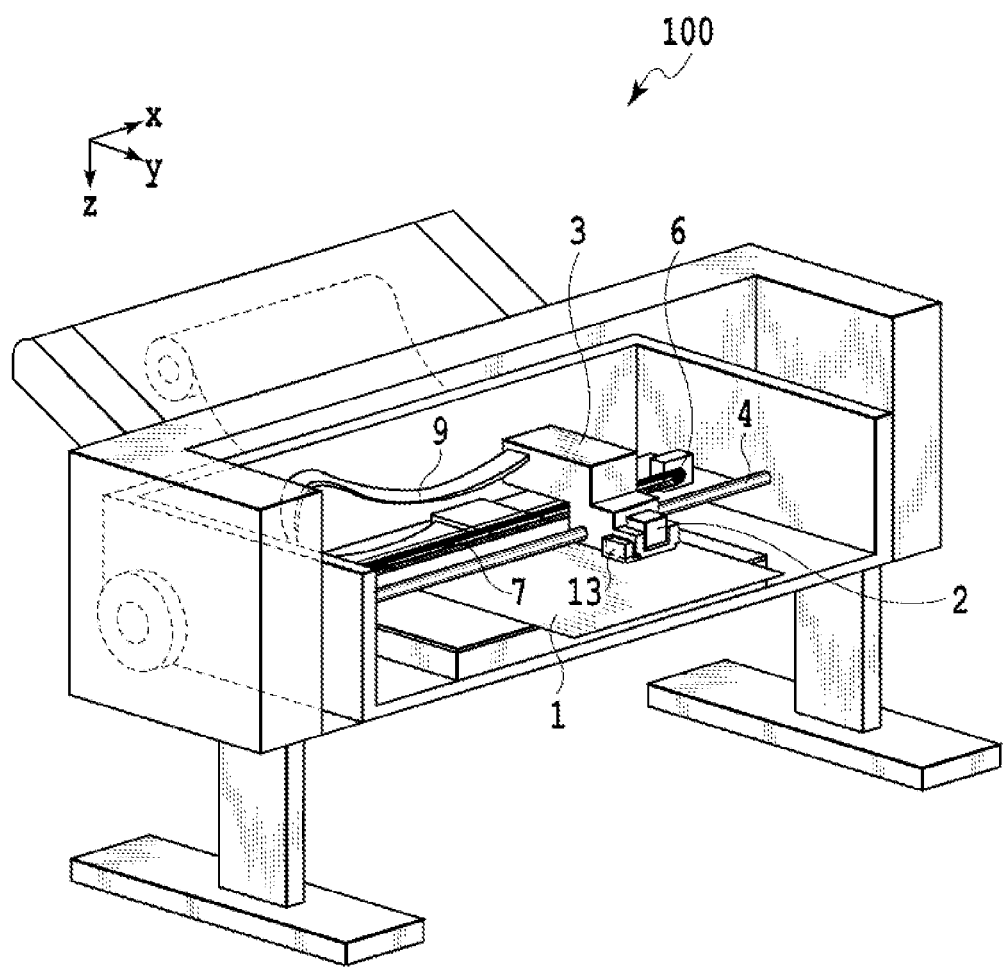
FIG. 1 is a perspective view showing an overall structure of an ink jet printing apparatus.

FIG. 1 is a perspective view showing an overall structure of an ink jet printing apparatus (hereinafter referred to as a "printing apparatus") 100 as a liquid ejection apparatus according to the present embodiment. The printing apparatus 100 according to the present embodiment is a serial scan type printing apparatus. As shown in this figure, the printing apparatus 100 is provided with a print head 2 as an ejection head, a carriage 3, a guide shaft 4, a timing belt 7, a flexible cable 9, and a sensor unit 13.

The print head 2 is provided with a plurality of ejection ports (not shown). A liquid is ejected from the ejection port in the direction shown by an arrow z (ejecting direction) in the figure so as to apply the liquid to a print medium 1 which is a medium. In the present embodiment, ink is used as a liquid. In addition, the meaning of a liquid herein includes an intermediate matter of a liquid and a solid.

The carriage 3 is slidably supported by the guide shaft 4, and is guided by the guide shaft 4 to move in a reciprocating manner in the x-direction (main scan direction) shown in the figure. A driving force transmitting mechanism such as a timing belt 7 transmits a driving force from a carriage motor (not shown) to the carriage 3, which makes the carriage 3 possible to move.

In the moving range of the carriage 3, a pulley (not shown) connected to the carriage motor is arranged at one end, and an idle pulley 6 is arranged at the other end. The timing belt 7 is stretched between the pulley (not shown) and the idle pulley 6, and the carriage 3 is coupled to the timing belt 7.

Furthermore, in order to prevent the carriage 3 from rotating about the guide shaft 4, the print apparatus 100 is provided with a support member (not shown) extending in parallel to the guide shaft 4. The carriage 3 is slidably supported also by the support member (not shown).

The carriage 3 is detachably equipped with the print head 2 and an ink tank (not shown). Ink is stored in the ink tank (not shown), and the ink is supplied to the print head 2 via a tube (not shown). In addition, although the present embodiment explains the case where the print head 2 and the ink tank (not shown) are separately provided, the print head 2 and the ink tank (not shown) may integrally constitute an ink cartridge.

Furthermore, the carriage 3 is equipped with an optical sensor unit 13. The sensor unit 13, that is a multi-sensor having a plurality of measuring functions, obtains optically information from the print medium 1. Furthermore, the sensor is configured including a light emitting element 22 and a light receiving element 23. The detailed description will follow with reference to FIG. 2.

The carriage 3 is connected via a flexible cable to an electric substrate (not shown) constituting a controller of the printing apparatus 100. This controls ejection of ink from each ejection port of the print head 2, and measurement by the sensor unit 13. Furthermore, an encoder sensor (not shown) reads a linear scale (not shown), so that information on the position of the carriage 3 is obtained.

A conveying motor (not shown) conveys the print medium 1 in the sub-scan direction (the direction shown by an arrow y in the figure) intersecting with the main scan direction (the direction shown by an arrow x in the figure). At the time of printing operation, the print head 2 performs a printing on the print medium 1 conveyed to a predetermined location by a conveying roller (not shown). More specifically, the print head 2 attached to the carriage 3 ejects ink to the print medium 1 at the appropriate timing in accordance with a print data as the carriage 3 moves in the x-direction. When the printing and scanning are completed, the print medium 1 is conveyed for a predetermined distance in the y-direction to execute the next printing and scanning.

In this manner, an image or a three-dimensional object is formed on the print medium 1 by alternately repeating the printing operation and the conveying operation.

Figure 2:
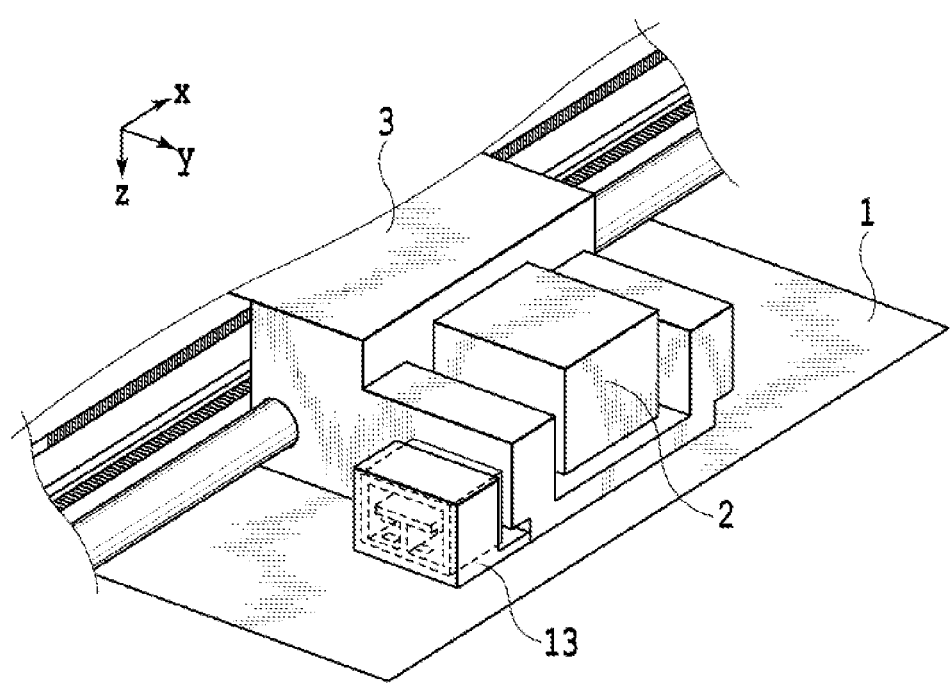
FIG. 2 is an expanded perspective view showing a structure on the periphery of a carriage.

FIG. 2 is an expanded perspective view showing a structure on the periphery of the carriage 3 shown in FIG. 1. As shown in this figure, the carriage 3 is equipped with the print head 2 and the sensor unit 13. The sensor unit 13 is attached to a side surface of the carriage 3 that is a front end or a backend in the moving direction of the carriage 3. The sensor unit 13 moves along with moving of the carriage 3 so as to be used to measure a concentration of a patch printed on the print medium 1, detection of an edge position on the print medium 1, detection of a pattern printed on the print medium 1, etc.

Figure 3A:
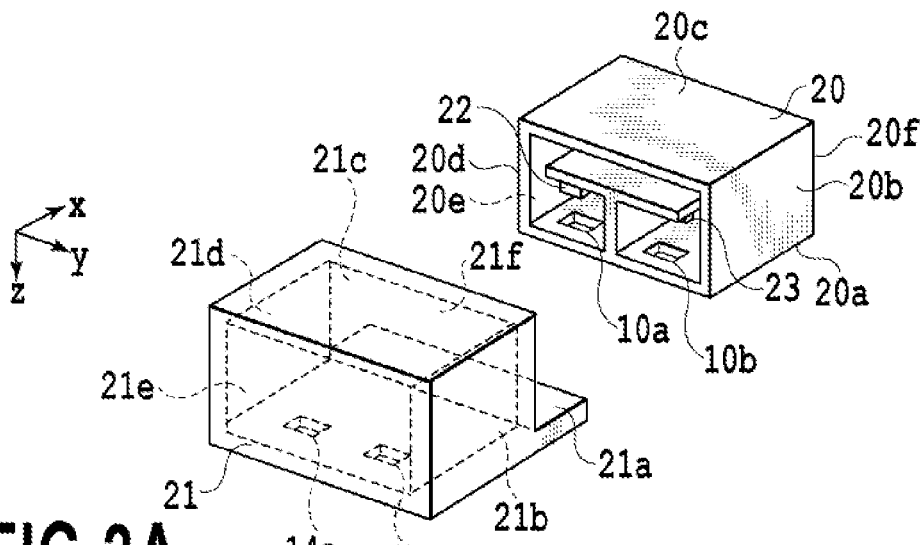
FIG. 3A is a diagram showing a structure of a sensor unit according to an embodiment.
Figure 3B:
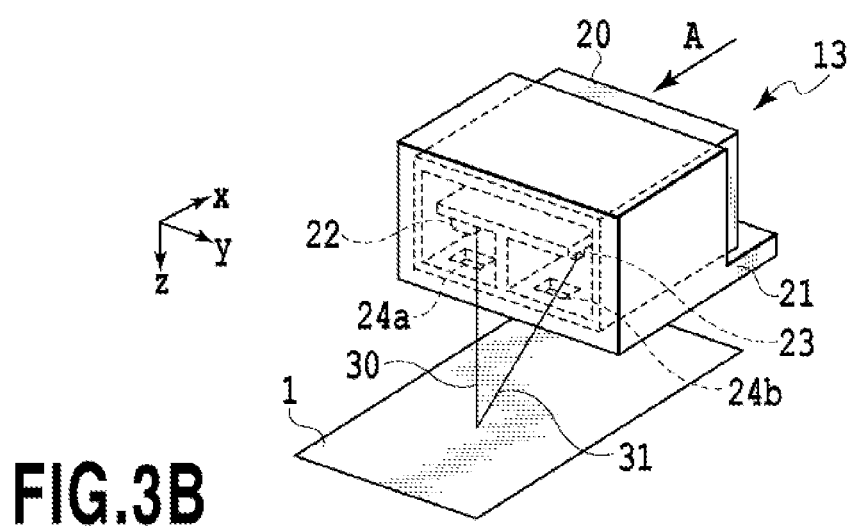
FIG. 3B is a diagram showing a structure of a sensor unit according to the embodiment.
Figure 3C:
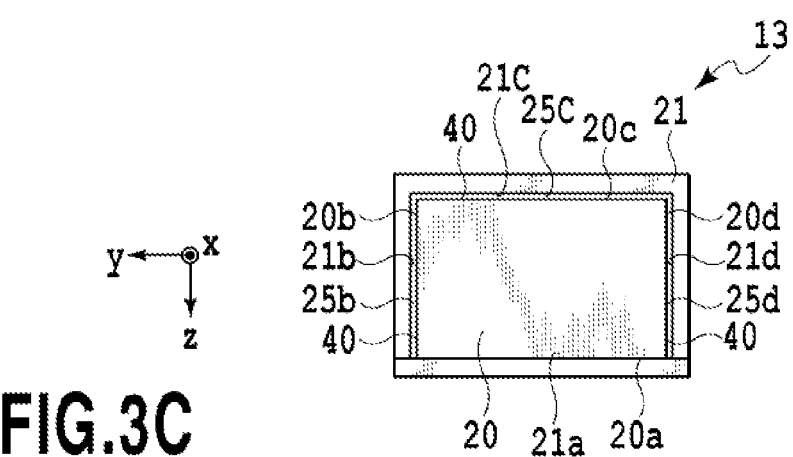
FIG. 3C is a diagram showing a structure of a sensor unit according to the embodiment.

FIGS. 3A to 3C are diagrams showing a structure of the sensor unit 13 according to the present embodiment. FIG. 3A is a perspective view showing each of a base part 20 and a cover part 21, and FIG. 3B is a perspective view showing the sensor unit 13 constituted by the base part 20 and a cover part 21. FIG. 3C is a diagram showing the sensor unit 13 viewing from the direction of an arrow A in FIG. 3B. In addition, FIGS. 3A and 3B, 7A and 7B, and 9A and 9B show the cover part 21, the inside of which is transparently viewed.

As shown in FIG. 3A, the base part 20 (a first part) has a space inside thereof, and thus the base part 20 contains the light emitting element 22 and the light receiving element 23.

Furthermore, the base part 20 is provided with an opening 10a and an opening 10b. In order not to block light emitted from the light emitting element 22, the opening 10a is provided at the position corresponding to the position where the light emitting element 22 is arranged. In order not to hinder the light receiving element 23 from receiving reflected light, the opening 10b is provided at the position corresponding to the position where the light receiving element 23 is arranged.

The cover part 21 (a second part) has a space inside thereof for arranging the base part 20. Furthermore, the cover part 21 is provided with an opening 14a and an opening 14b. The opening 14a is provided at the position corresponding to the opening 10a of the base part 20 when the cover part 21 is combined with the base part 20, and the opening 14b is provided at the position corresponding to the opening 10b of the base part 20.

The base part 20 of the present embodiment has a shape of substantially rectangular parallelepiped. When the upstream side in the z-direction shown in the figure is defined as the upper side, the base part 20 has a surface 20c as being a top surface, a surface 20a as being a bottom surface, a surface 20f as being a back surface, a surface 20e as being a front surface, a surface 20d as being a side surface on the upstream side in the y-direction, and a surface 20b as being a side surface on the downstream side in the y-direction. In the present embodiment, the surface 20e is opened.

Furthermore, the cover part 21 of the present embodiment also has a shape of substantially rectangular parallelepiped. The cover part 21 has surfaces 21a to 21f which are inner surfaces respectively facing the surfaces 20a to 20f of the base part 20 when combined with the base part 20. The surface 21f is opened which is an entrance for the base part 20 at the time of combining the base part 20 with the cover part 21.

In the present embodiment, the size of an inner dimension the cover part 21 is larger than the size of an outer dimension of the base part 20, so that the base part 20 is partially accommodated in the inside of the cover part 21. When the base part 20 and the cover part 21 are engaged with each other, the surface 20e that is an opening surface of the base part 20 is opposed to the surface 21f that is an opening surface of the cover part 21, so that the base part 20 is inserted into the cover part 21.

As shown in FIG. 3B, the sensor unit 13 is configured including the base part 20 and the cover part 21. As shown in FIG. 3B, when the base part 20 and the cover part 21 are combined with each other, the openings 10a and 14a form a light path opening 24a which forms a light path between the sensor and the outside, and the openings 10b and 14b form a light path opening 24b. Therefore, the print medium 1 is irradiated with light 30 emitted from the light emitting element 22 via the light path opening 24a, and light 31 reflected at the print medium 1 is received at the light receiving element 23 via the light path opening 24b.

In the present embodiment, the base part 20 and the cover part 21 are engaged with each other so that a clearance is formed between the base part 20 and the cover part 21. More specifically, in the present embodiment, the base part 20 and the cover part 21 are combined with each other so that the surface 20a of the base part 20 is brought into intimate contact with the surface 21a of the cover part 21 and the other surfaces do not come into contact with one another. Therefore, a clearance is provided between each of the outer surfaces of the base part 20 other than the surface 20a and each of the inner surfaces of the cover part 21 other than the surface 21a.

As shown in FIG. 3C, clearances 25b to 25d are provided between the surface 20b and a surface 21b, the surface 20c and the surface 21c, and the surface 20d and the surface 21d, respectively. Furthermore, although not shown in FIG. 3C, a clearance 25e is provided between the surface 20e and the surface 21e. In the present embodiment, a ventilation opening, which is a hole 40 configured by the clearances 25b to 25e, is formed on the sensor unit 13. The hole 40 is communicated with the light path openings 24a and 24b.

In the present embodiment, forming the hole 40 suppresses the amount of ink mist adhering to the light emitting element 22 and the light receiving element 23. More specifically, an air flow is generated which enters from the hole 40 into the inside of the sensor unit 13, and then exits from the light path openings 24a and 24b. An air containing ink mist is prevented from flowing from the light path openings 24a and 24b toward the light emitting element 22 and the light receiving element 23. This reduces the amount of ink mist adhering to the light emitting element 22 and the light receiving element 23. An air flow at the time of scanning of the carriage 3 will be described below in detail with reference to FIGS. 12A and 12B.

Figure 4:
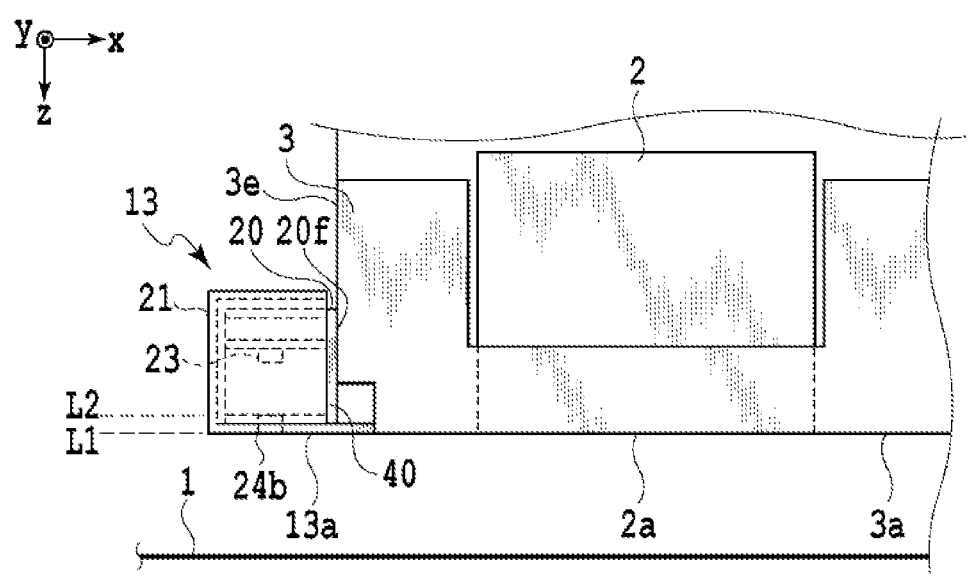
FIG. 4 is a diagram showing a state where the sensor unit according to the embodiment is attached to a carriage.
Figure 8:
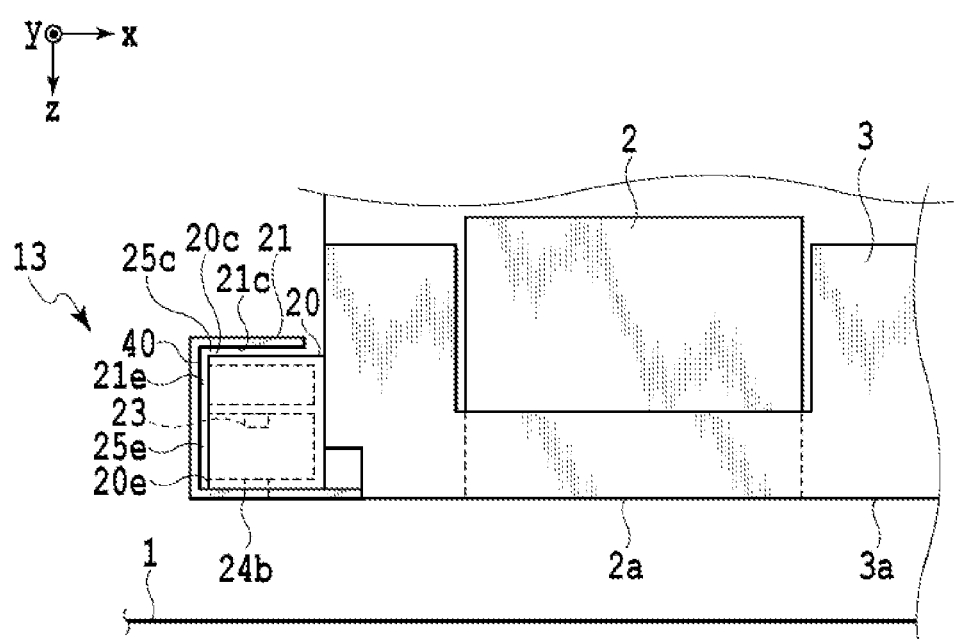
FIG. 8 is a diagram showing a state where the sensor unit according to the first variation is attached to a carriage.
Figure 10:
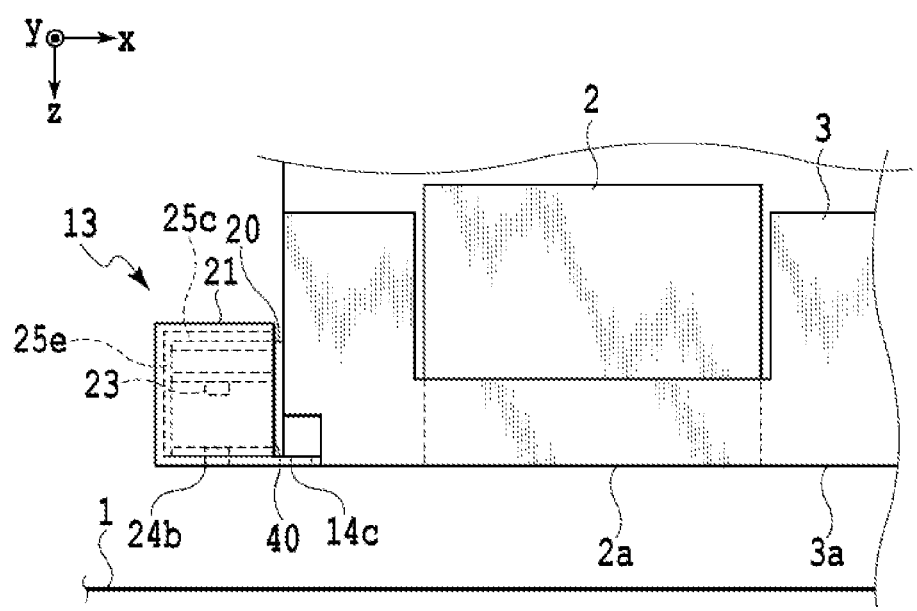
FIG. 10 is a diagram showing a state where the sensor unit according to the second variation is attached to a carriage.

FIG. 4 is a diagram showing a state where the sensor unit 13 according to the present embodiment is attached to the carriage 3. FIGS. 4, 8, and 10 show a state of the carriage 3 viewing from the downstream side in the y-direction shown in FIG. 1. In addition, FIGS. 4 and 10 show the carriage 3, the sensor unit 13, the cover part 21, and the base part 20, the inside of which are transparently viewed.

As shown in FIG. 4, in the present embodiment, the surface 20f of the base part 20 is brought into intimate contact with an attachment surface 3e which is a side surface on the upstream side in the x-direction of the carriage 3, so that the sensor unit 13 is attached to the carriage 3. Therefore, the sensor unit 13 is attached on the upstream side in the x-direction from the position where the print head 2 is mounted to the carriage 3, i.e., on the rearward side in the direction shown by an arrow x in the figure.

As shown in FIG. 4, in the present embodiment, the hole 40 of the sensor unit 13 is opened toward the downstream side in the x-direction, i.e., the direction facing the attachment surface 3e and the position where the print head 2 is mounted. More specifically, in the present embodiment, the clearances 25b to 25d are opened in the direction toward the attachment surface 3e, and all of the hole 40 formed by the clearances 25b to 25d is opened in the direction toward the attachment surface 3e.

This makes it possible to take an air flowing from the side of the attachment surface 3e in the hole 40 of the sensor unit 13 when the sensor unit 13 is at the tail in the moving direction of the carriage 3 while the carriage 3 is moving, and then discharge the air from the light path openings 24a and 24b.

Furthermore, as shown in FIG. 4, the hole 40 is provided on the upstream side in the z-direction from an ejection opening surface 2a on which the ejection opening of the print head 2 is formed. More specifically, a line L2 indicating the position of the hole 40 on the downstream side in the z-direction is located on the upstream side in the z-direction from a line L1 indicating the position of the ejection opening surface 2a. In the present embodiment, the hole 40 is set to be opened in the direction toward the attachment surface 3e, and the position of the hole 40 in the z-direction is set to be on the upstream side in the z-direction from the position of the ejection opening surface 2a. Therefore, an air, which flows in a space except that between the ejection opening surface 2a and the print medium 1 and contains little ink mist, is taken in the hole 40, and the air is discharged from the light path openings 24a and 24b.

Generation of the air flow makes it possible to reduce the amount of ink mist adhering to the sensor. More specifically, the air containing little ink mist is used to generate the air flow discharged from the light path openings 24a and 24b to the outside of the sensor unit 13, so that the air containing ink mist is prevented from entering from the light path openings 24a and 24b into the sensor unit 13. Since the air flowing in the sensor unit 13 contains little ink mist, it is possible to reduce the amount of ink mist adhering to the sensor compared to the case where the air containing ink mist enters into the sensor unit 13.

Furthermore, as shown in FIG. 4, in the present embodiment, intervals substantially same size as one another are provided between a bottom surface 3a that is a surface of the carriage 3 on the downstream side in the z-direction and the print medium 1, between the bottom surface 13a of the sensor unit 13 and the print medium 1, and between the ejection opening surface 2a of the print head 2 and the print medium 1. Therefore, the bottom surface 3a, the bottom surface 13a, and the ejection opening surface 2a are arranged to be substantially flush with one another.

In this manner, the surface opposite to the print medium 1 is made to be substantially planar, so that the air flow containing ink mist is prevented from becoming turbulent between the print medium 1 and the ejection opening surface 2a. This makes it possible to stabilize the velocity of air flow between the print medium 1 and the ejection opening surface 2a without disturbance, and to reduce the amount of air entering from the light path openings 24a and 14b into the sensor unit 13.

Figure 5:
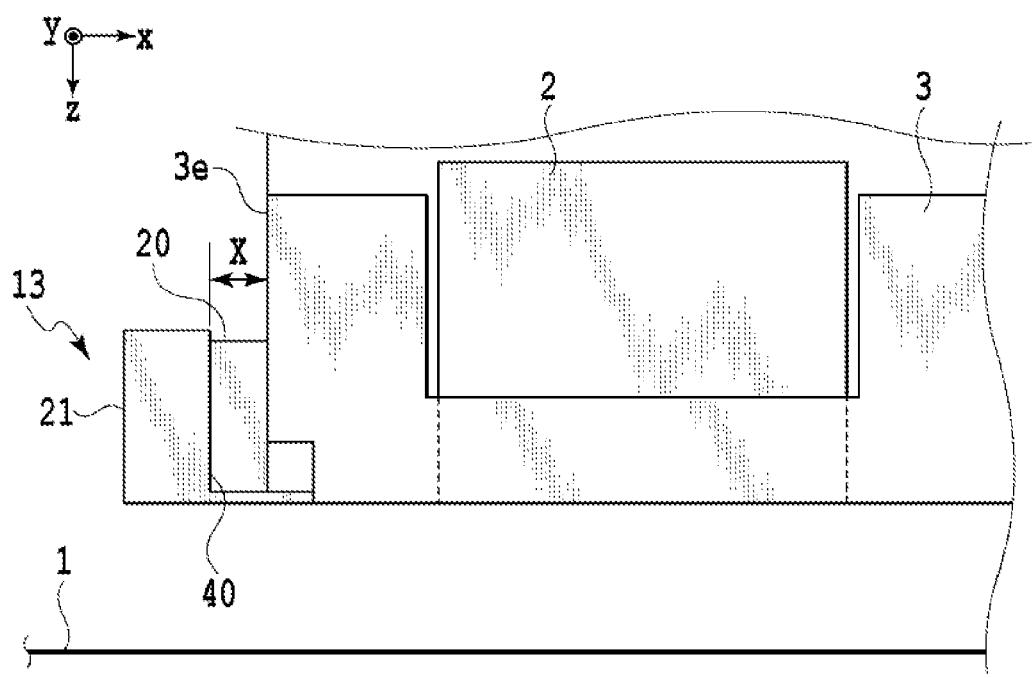
FIG. 5 is a diagram for explaining the distance between an opening end of a hole and a side surface of the carriage.

FIG. 5 is a diagram for explaining the distance between the side surface of the cover part 21 and the side surface of the carriage 3. FIG. 5 shows a distance X from the attachment surface 3e of the carriage 3 to an opening end of the hole 40 that is formed by the cover part 21 and the base part 20. The distance X has been herein set to be 0 mm, 5 mm, 10 mm, and 15 mm, and the number of adhesion (the amount of adhesion) of ink mist has been compared for each distance to determine the optimal distance X in which the amount of adhered ink mist is small. The result thereof is shown in FIG. 6.

Figure 6:
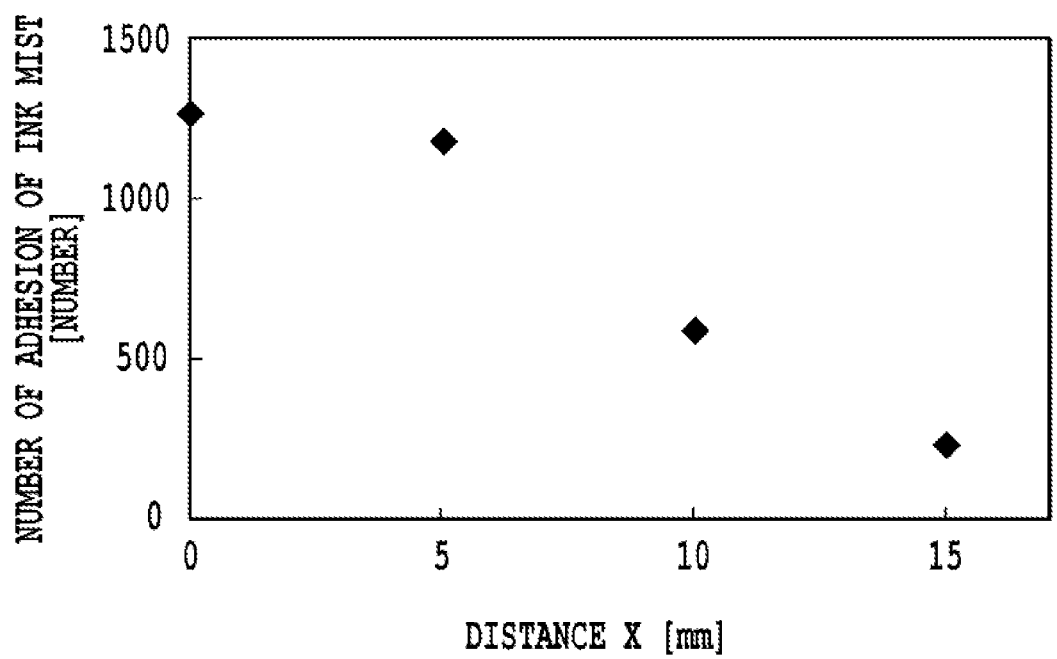
FIG. 6 is a graph showing the relation between the distance shown in FIG. 5 and the amount of adhered mist.

FIG. 6 is a graph showing the relation between the distance X shown in FIG. 5 and the number of adhered mist. In the graph shown in FIG. 6, the vertical axis represents the number of adhered ink mist, and the horizontal axis represents the distance X. The number of adhered ink mist has been determined herein by covering the light emitting element 22 and the light receiving element 23 with glossy paper and affixing the paper so as to count the number of ink mist adhered to the glossy paper.

As shown in FIG. 6, the number of adhered ink mist is about 1250 when the distance X is 0 mm, and the number of adhered ink mist is about 1100 when the distance X is 5 mm. Furthermore, the number of adhered ink mist is about 600 when the distance X is 10 mm, and the number of adhered ink mist is about 250 when the distance X is 15 mm. In this manner, when the distance X is set to be 10 mm or more, the number of adhered ink mist could be suppressed to about 50% or less compared to the case where the distance X is set to be 0 mm. It would appear that this is because the air flow generated inside the printing apparatus 100 by the scanning of the carriage 3 does not enter into the opening end of the hole 40 if the distance X is not a certain distance.

Accordingly, in the structure of the present embodiment, the opening end of the hole 40 is provided at the position where the distance X is 10 mm or more, i.e., at the position away from the attachment surface 3e by 10 mm or more. In addition, the structure different from the present embodiment makes it possible to reduce the number of adhered ink mist by setting the distance X suitable for the structure concerned.

Two variations of the present embodiment will be described below, and the description will be made regarding the air flow inside the printing apparatus 100 in the structure of the present embodiment and those of the variations.
(First Variation)

In a first variation, the hole 40 is formed by clearances 25c to 25e. Other structures are the same as those in the embodiment, and thus the explanation thereof will be omitted.

Figure 7A:
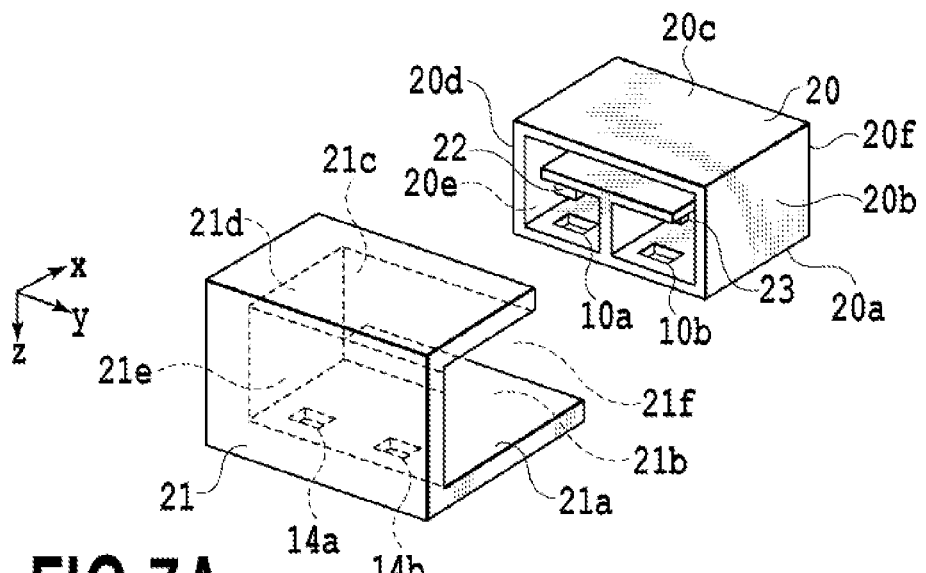
FIG. 7A is a diagram showing a structure of a sensor unit of a first variation.
Figure 7B:
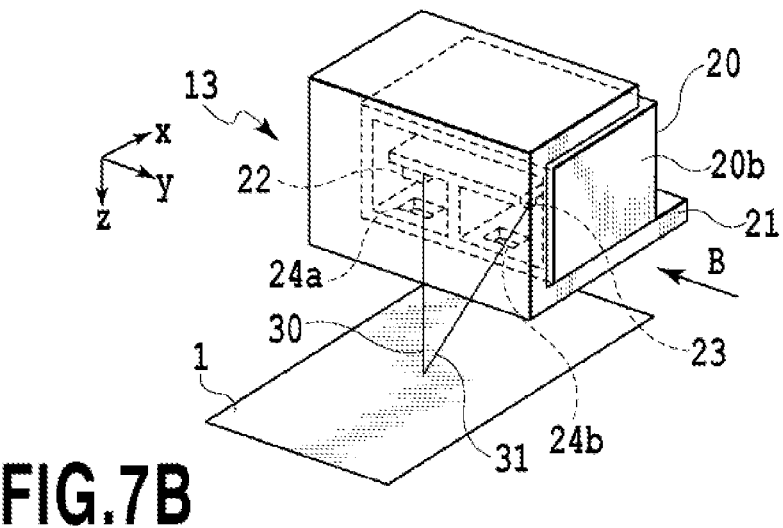
FIG. 7B is a diagram showing a structure of a sensor unit of the first variation.
Figure 7C:
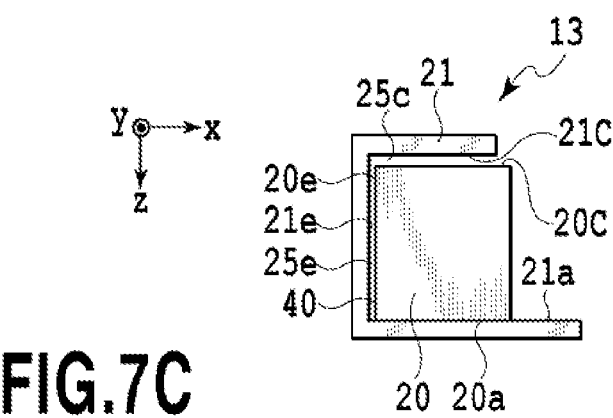
FIG. 7C is a diagram showing a structure of a sensor unit of the first variation.

FIGS. 7A to 7C are diagrams showing the structure of the sensor unit 13 according to the first variation. FIG. 7A is a perspective view showing each of the base part 20 and the cover part 21, and FIG. 7B is a perspective view showing the sensor unit 13 constituted by the base part 20 and the cover part 21. FIG. 7C is a diagram showing the sensor unit 13 viewing from the direction of an arrow B in FIG. 7B.

As shown in FIG. 7A, in the first variation, a side surface on the downstream side in the y-direction of the cover part 21 is opened. More specifically, in the first variation, no wall is formed on the downstream side in the y-direction of the cover part 21, and thus the inner wall 21b is not provided. Therefore, as shown in FIG. 7B, the base part 20 and the cover part 21 fit together results in exposure of the surface 20b of the base part 20.

Also in the first variation, similar to the embodiment, the base part 20 and the cover part 21 are combined with each other so that the surface 20a of the base part 20 is brought into intimate contact with the surface 21a of the cover part 21 and the other surfaces do not come into contact with one another. Furthermore, in the first variation, the base part 20 and the cover part 21 are combined with each other so that the surface 20b of the base part 20 is arranged to be substantially flush with the end on the downstream side in the y-direction of the cover part 21. Therefore, the hole 4 in the first variation is formed by the clearances 25c and 25e shown in FIG. 7C, and a clearance 25d not shown in FIG. 7C.

The state shown in FIG. 8 is caused when the sensor unit 13 shown in FIGS. 7B and 7C is attached to the carriage 3.

FIG. 8 is a diagram showing a state where the sensor unit 13 according to the first variation is attached to the carriage 3. In addition, FIG. 8 shows the state where the inside of the base part 20 is transparently viewed. As shown in FIG. 8, the first variation takes the structure in which an opening of the clearance 25e is opened toward the downstream side in the y-direction. More specifically, the hole 40 in the first variation is opened in the direction toward the attachment surface 3e and the direction intersecting with the direction concerned.

In this manner, even if the hole 40 having different opening direction is formed on the sensor unit 13, an air flow is generated which enters from the hole 40 into the sensor unit 13, and exits through the light path openings 24a and 24b to the outside the sensor unit 13. This makes it possible to hinder the air flow from the light path openings 24a and 24b into the sensor unit 13 toward the light emitting element 22 and the light receiving element 23, and thus to reduce the amount of ink mist adhering to the light emitting element 22 and the light receiving element 23, even in the first variation.
(Second Variation)

In the second variation, the sensor unit 13 is provided with an opening 14c. Other structures are the same as those in the embodiment, and thus the explanation thereof will be omitted.

Figure 9A:
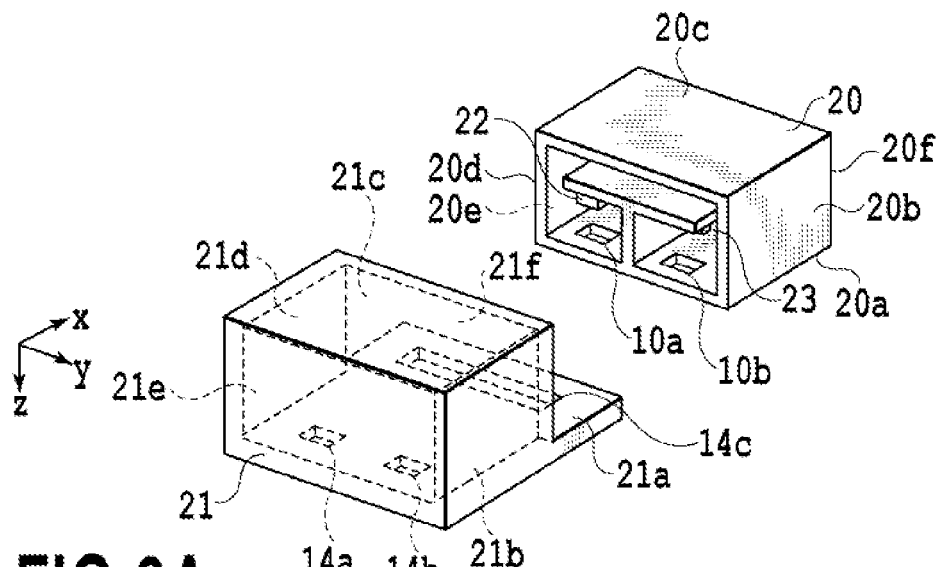
FIG. 9A is a diagram showing a structure of a sensor unit of a second variation.
Figure 9B:
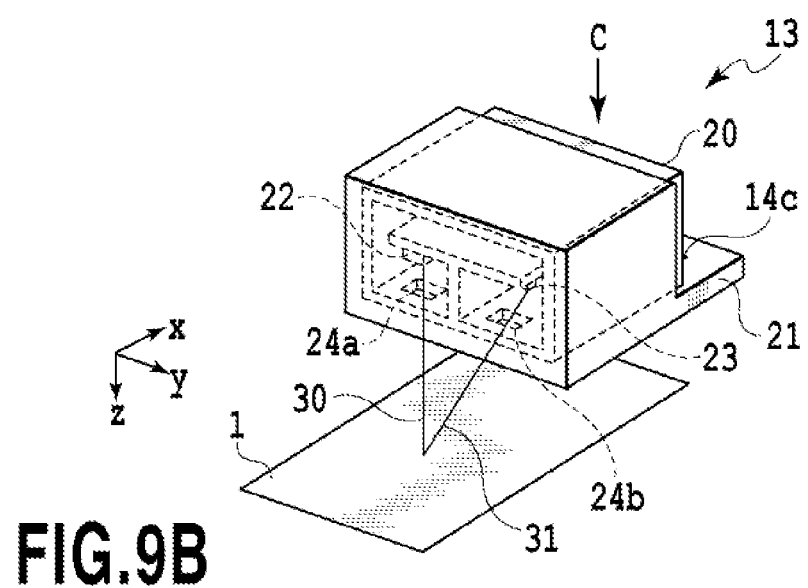
FIG. 9B is a diagram showing a structure of a sensor unit of the second variation.
Figure 9C:
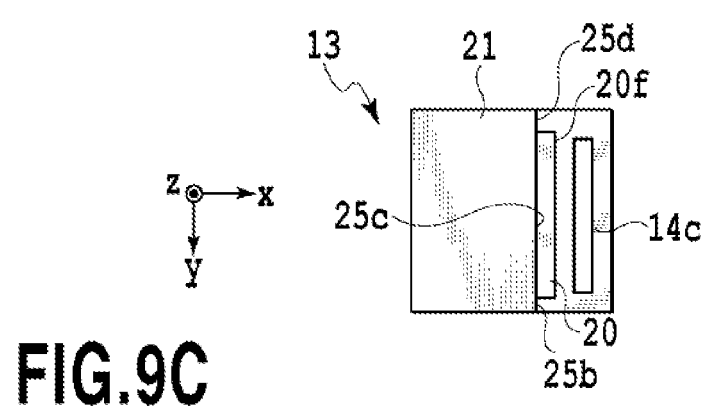
FIG. 9C is a diagram showing a structure of a sensor unit of the second variation.

FIGS. 9A to 9C are diagrams showing the structure of the sensor unit 13 according to the second variation. FIG. 9A is a perspective view showing each of the base part 20 and the cover part 21, and FIG. 9B is a perspective view showing the sensor unit 13 constituted by the base part 20 and the cover part 21. FIG. 9C is a diagram showing the sensor unit 13 viewing from the direction of an arrow C in FIG. 9B.

As shown in FIG. 9A, in the second variation, an opening 14c is formed also a surface of the cover part 21 on which the openings 14a and 14b are formed. The opening 14c is used as a ventilation opening similar to the hole 40, so that it is possible to enlarge the opening area of the ventilation opening for taking an air into the sensor unit 13 compared to the structure of the embodiment.

As shown in FIG. 9A, in the second variation, the opening 14c is provided along the longitudinal direction of the cover part 21 (the y-direction shown in figure). The state shown in FIG. 9B is caused when the base part 20 and the cover part 21 are combined with each other. When viewing the sensor unit 13 from the direction shown by an arrow C in FIG. 9B, the opening 14c is arranged on the downstream side in the x-direction from the surface 20f which is the side surface of the base part 20 on the downstream side in the x-direction as shown in FIG. 9C.

FIG. 10 is a diagram showing a state where the sensor unit 13 according to the second variation is attached to the carriage 3. As shown in FIG. 10, in the second variation, the second variation is provided with the opening 14c on the downstream side in x-direction from the opening end of the hole 40. Furthermore, in the z-direction, the opening end 14c is provided at the substantially same position of the ejection opening surface 2a. In this manner, in the second variation, the opening 14c is provided in addition to the hole 40 in the embodiment, so that an air flow is generated which enters from the opening 14c into the sensor unit 13 and then exits from the light path openings 24a and 24b.

In this manner, an air entering from the opening 14c into the sensor unit 13 is discharged from the light path openings 24a and 24b also in the case where the sensor unit 13 has the opening end 14c provided at the substantially same position of the ejection opening surface 2a in the z-direction. Thereby, also in the second variation, the air flow is prevented from entering from the opening 14c into the sensor unit 13 toward the light emitting element 22 and the light receiving element 23, thereby reducing the amount of ink mist adhering to the light emitting element 22 and the light receiving element 23.
(Air Flow in the Printing Apparatus 100)

Figure 11:
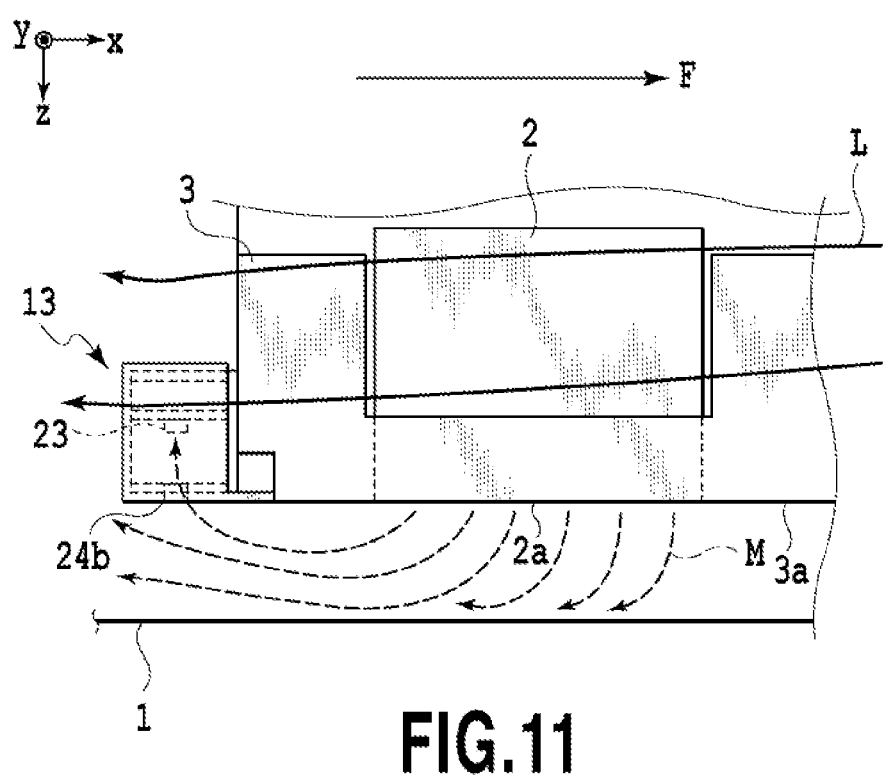
FIG. 11 is a diagram showing airflow upon using a sensor unit on which no hole is formed.

FIGS. 11, 12A, 12B, 13A, and 13B are diagrams showing an air flow within the printing apparatus 100 while the carriage 3 is moving. FIG. 11 shows the air flow within the printing apparatus 100 in the case of using the sensor unit 13 in which the hole 40 is not formed, and shows the air flow when the carriage 3 moves from the upstream side in the x-direction toward the downstream side (in the F direction (forward direction) in the figure).

Figure 12A:
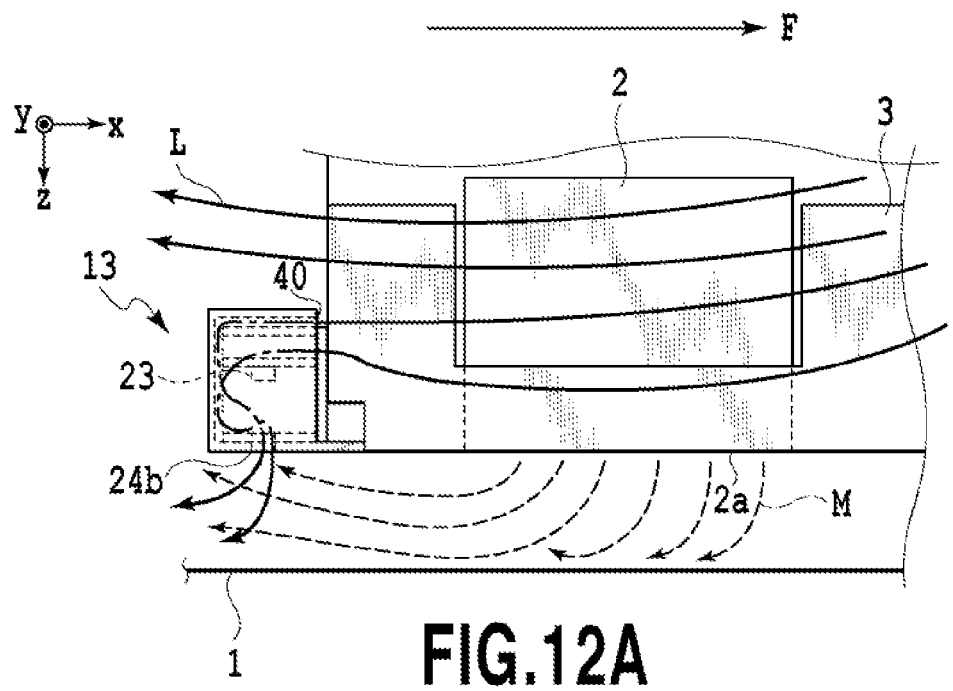
FIG. 12A is a diagram showing airflow within a printing apparatus according to the embodiment.
Figure 12B:
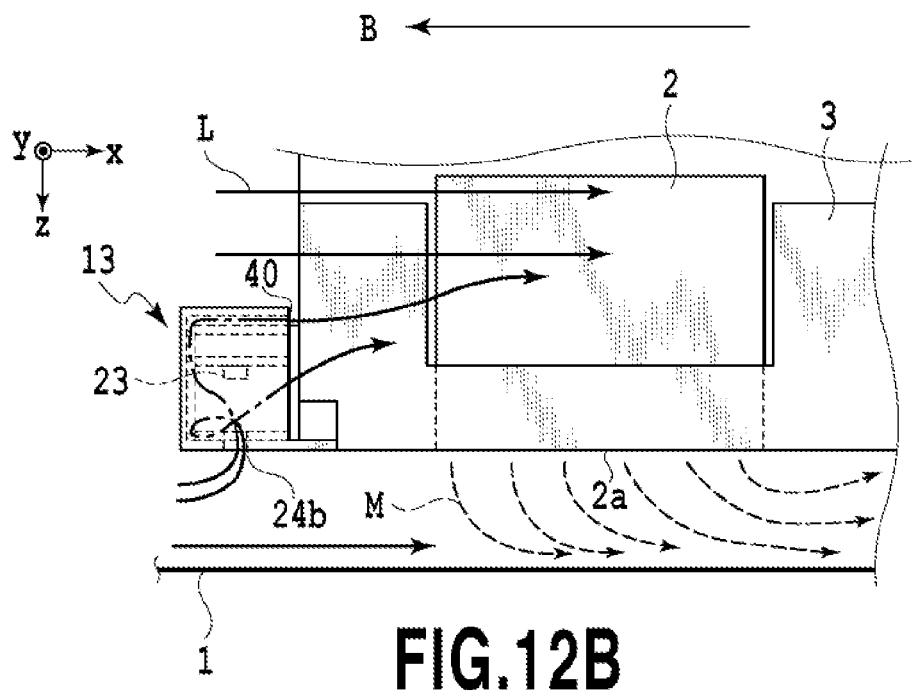
FIG. 12B is a diagram showing airflow within a printing apparatus according to the embodiment.

FIG. 12A shows the air flow within the printing apparatus 100 in the case of using the sensor unit 13 according to the present embodiment, and shows the air flow when the carriage 3 moves in the F direction. FIG. 12B shows the air flow within the printing apparatus 100 in the case of using the sensor unit 13 according to the present embodiment, and shows the air flow when the carriage 3 moves from the downstream side in the x-direction toward the upstream side (in the B direction (backward direction) in the figure).

Figure 13A:
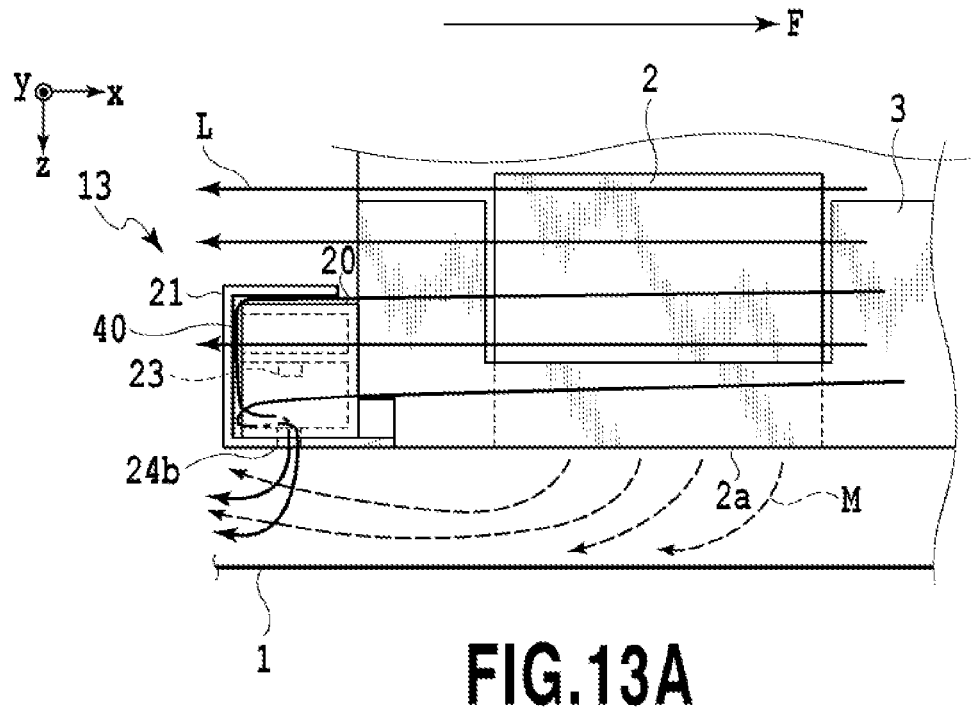
FIG. 13A is a diagram showing airflow within a printing apparatus according to the first variation.
Figure 13B:
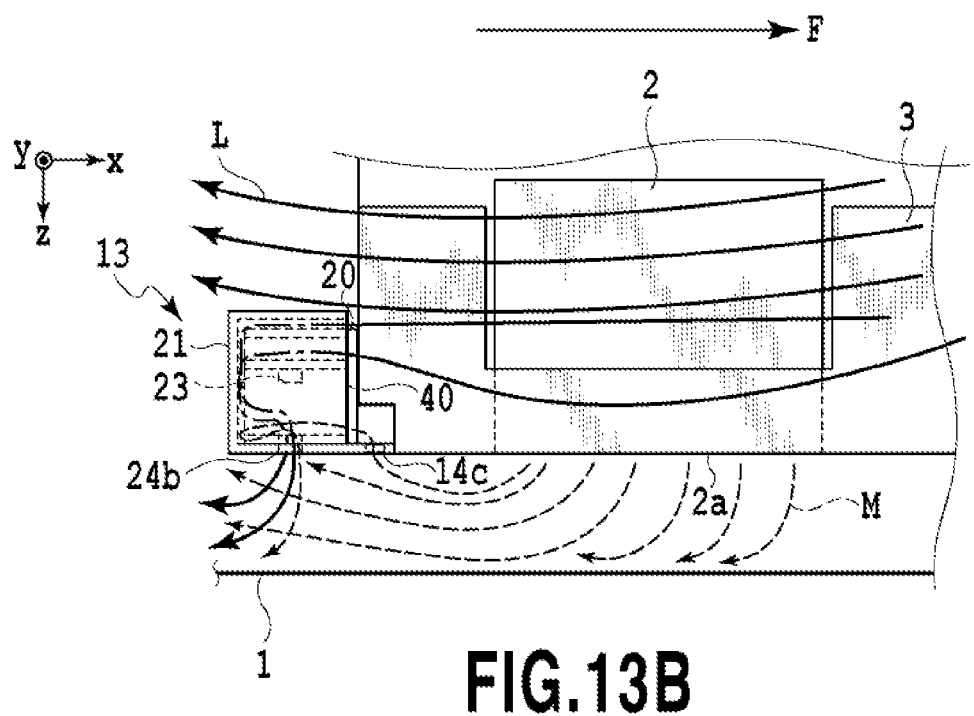
FIG. 13B is a diagram showing airflow within a printing apparatus according to the second variation.

FIG. 13A shows the air flow within the printing apparatus 100 in the case of using the sensor unit 13 according to the first variation, and shows the air flow when the carriage 3 moves in the F direction. FIG. 13B shows the air flow within the printing apparatus 100 in the case of using the sensor unit 13 according to the second variation, and shows the air flow when the carriage 3 moves in the F direction.

Ink is ejected from the ejection opening of the print head 2 while the carriage 3 moves in the main scanning direction. Thereby, due to the effect of the air flow generated by the moving of the carriage 3, the air containing ink mist which is generated by ejection of the ink from the ejection opening of the print head 2 flows in the direction opposite to the moving direction of the carriage 3. The air flow M flowing in the space between the ejection opening surface 2*a* and the print medium 1 contains ink mist generated from the ejection opening, whereas an air flow L flowing in the space other than the space between the ejection opening surface 2*a* and the print medium 1 contains almost no ink mist.

In the case where the hole 40 is not formed on the sensor unit 13, the air flow M containing ink mist may enter from the light path openings 24*a* and 24*b* into the sensor unit 13 toward the light emitting element 22 and the light receiving element 23, as shown in FIG. 11. Furthermore, in this case, the air flow L has little influence on the flow of the air flow M from the light path openings 24*a* and 24*b* toward the light emitting element 22 and the light receiving element 23.

Therefore, the air flow L does not block the air flow M flowing toward the light emitting element 22 and the light receiving element 23, the ink mist contained in the air flow M may adhere to the light emitting element 22 and the light receiving element 23.

In contrast, in the present embodiment, even if the flow of the air flow M toward the light path openings 24*a* and 24*b* is generated, the flow of the air flow L discharged from the hole 40 to the light path openings 24*a* and 24*b* is generated, thereby blocking the flow of the air flow M toward inside the sensor unit 13.

As shown in FIG. 12A, the air flow L entering from the opening end of the hole 40 into the sensor unit 13 causes an air flow into the sensor unit 13, and the air is circulated inside the sensor unit 13 and then discharged from the light path openings 24*a* and 24*b*. In other words, in the present embodiment, the air inside the printing apparatus 100 is collected from the opening end of the hole 40 to the inside of the sensor unit 13 to increase the pressure inside the sensor unit 13, and then the air is discharged from the light path openings 24*a* and 24*b*.

This hinders the flow of the air containing ink mist from the light path openings 24*a* and 24*b* toward the sensor unit 13. Furthermore, as described above, since the air flow L contains almost no ink mist, the ink mist hardly adheres to the light emitting element 22 and the light receiving element 23 even though the air flow L passes through the sensor unit 13. Accordingly, in the structure of the present embodiment, it is possible to reduce the amount of ink mist adhering to the light emitting element 22 and the light receiving element 23 compared to the case where the air flow M enters into the sensor unit 13 without being blocked by the air flow L.

In addition, the adhesion of ink mist to the light emitting element 22 and the light receiving element occurs relatively frequently in the case where the moving direction of the carriage 3 is the direction shown in FIG. 12A, i.e., the sensor unit 13 is at the tail in the moving direction of the carriage 3.

On the other hand, as shown in FIG. 12B, when the sensor unit 13 is at the head in the moving direction of the carriage 3, the air flow M flows in the direction opposite to the moving direction of the carriage 3.

Therefore, the air flow M does not reach the light path openings 24*a* and 24*b* of the sensor unit 13 which is located at the head in the moving direction of the carriage 3. Furthermore, as shown in FIG. 12B, the air flow L causes an air enter from the light path openings 24*a* and 24*b* into the sensor unit 13, and then exit from the hole 40. The air flow L contains almost no ink mist as described above. Therefore, the ink mist hardly adheres to the light emitting element 22 and the light receiving element 23.

Therefore, in the present embodiment, the opening direction of the hole 40 is the direction toward the head of the moving direction when the sensor unit 13 is located at the tail relative to the moving direction of the carriage 3.

As shown in FIG. 13A, in the case of the structure of the first variation, the air flow L enters from the opening end of the holes 40, which are the opening ends of the clearances 25*c* and 25*e* (shown in FIG. 13A), and the clearance 25*d* (not shown in FIG. 13A), into the sensor unit 13. The air caused by the air flow L is circulated inside the sensor unit 13 and then discharged from the light path openings 24*a* and 24*b*.

In the first variation, the opening direction of the hole 40 is the direction toward the attachment surface 3*e*, and the direction intersecting the direction described above and toward the downstream side in the direction of carrying the print medium 1. In this manner, even in the case of forming the holes 40 having openings opened in the different direction from one another, the flow of air discharged from the light path openings 24*a* and 24*b* is generated, thereby blocking the flow of the air entering from the light path openings 24*a* and 24*b* into the sensor unit 13. Thereby, it is possible to reduce the amount of ink mist adhering to the sensor compared to the case where the hole 40 is not formed on the sensor unit 13.

As shown in FIG. 13B, in the case of the second variation, the air flow L enters from the opening end of the hole 40 into the sensor unit 13, and the air flow M also enters from the opening 14*c* into the sensor unit 13. The air flows L and M are circulated inside the sensor unit 13 and then discharged from the light path openings 24*a* and 24*b*.

Here, the air flow M containing ink mist also flows into the sensor unit 13. However, the air flow M concerned is discharged along with the air flow L from the light path openings 24*a* and 24*b*, so that it is possible to prevent the other air flow M from entering from the light emitting openings 24*a* and 24*b* into the sensor unit 13. Therefore, it is possible to reduce the amount of ink mist adhering to the light emitting element 22 and the light receiving element 23.

Next, the description will be made regarding the method for verifying the amount of adhered ink mist which has been actually carried out for each structure of sensor unit of the embodiment, the first variation, and the second variation, and the results thereof. First, the method for verifying will be described. In order to determine the amount of ink mist adhering to the light emitting element 22 and the light receiving element 23, the light emitting element 22 and the light receiving element 23 are covered with glossy paper, the glossy paper is affixed to the light emitting element 22 and the light receiving element 23, in the same way as described in FIG. 6. Then, printing was conducted for a predetermined period of time, and then the ink droplets adhered to the glossy paper was magnified using a microscope to count the number of ink droplets.

As a result, given that the number of ink droplets adhered to glossy paper in the structure of the embodiment is G, the number of ink droplets adhered to glossy paper in the structure of the first variation is H, and the number of ink droplets adhered to glossy paper in the structure of the second variation is I, the obtained results have been as follows:

G=228;
H=2705; and
I=1992.

As a result thereof, it is G<H, and thus it has been found that the structure of the embodiment reduces the larger amount of ink mist adhered to the sensor than the structure of the first variation. More specifically, it has been found that the structure in which the hole 40 is opened as a whole in the direction facing the attachment surface 3e reduces the larger amount of ink mist adhered to the sensor than the structure in which the hole 40 has different opening direction.

Furthermore, it is G<I, and thus it has been found that the structure of the embodiment reduces the larger amount of ink mist adhered to the sensor than the structure of the second variation. More specifically, it has been found that the structure in which all the ventilation openings are located on the upstream side in the z-direction from the ejection opening surface 2a reduces the larger amount of ink mist adhered to the sensor than the structure of providing the ventilation opening such as the opening 14c at the substantially same location as the ejection opening surface 2a.

Accordingly, it has been verified that the structure of the embodiment reduces the larger amount of ink mist adhered to the sensor than the structure of the first variation and the structure of the second variation.

Furthermore, it is I<H, and thus it has been found that the structure of the second variation reduces the larger amount of ink mist adhered to the sensor than the structure of the first variation.

As a method for suppressing the amount of ink mist adhering to the sensor, a method may be possible such as providing a member for blocking the light path opening when the sensor is not used, or making the distance between the sensor and the light path opening relatively longer. However, if a member for blocking the light path opening is provided, newly providing the member and a mechanism for driving the member may cause upsizing the sensor unit and increase in cost. Furthermore, if the distance between the sensor and the light path opening is made relatively longer, the detection accuracy of the sensor may be degraded.

In contrast, as described above, the present embodiment generates the air reversely flows against the air flow entering from the light path opening into the sensor unit, so that the amount of ink mist adhering to the sensor is reduced. Therefore, in the present embodiment, it is possible to suppress the amount of ink mist adhering to the sensor without upsizing the sensor unit and increase in cost due to the installation of a new mechanism for blocking the light path opening. Furthermore, in the present embodiment, it is possible to suppress the amount of ink mist adhering to the sensor without degrading the detection accuracy of the sensor due to the large distance taken between the sensor and the light path opening.

(Others)

Although the embodiment described above has described the structure in which the sensor unit 13 is attached on one side surface in the moving direction of the carriage 3, the sensor unit 13 may be attached on both the side surfaces in the moving direction of the carriage 3.

Furthermore, the embodiment described above has described the structure in which the sensor unit 13 is attached on the upstream side in the direction shown by an arrow x in the figure relative to the carriage 3 when seeing the carriage 3 from the downstream side in the y-direction. However, the sensor unit 13 may be attached on the opposite side surface, i.e., the downstream side in the x-direction relative to the carriage 3

In any case, the sensor unit 13 is provided with an opening opened toward the attachment surface 3e of the carriage 3, so that it is possible to reduce the amount of ink mist adhering to the sensor compared to the structure of having no opening.

The embodiment described above has described the structure in which the sensor unit 13 is attached to the side surface in the moving direction of the carriage 3. However, the sensor unit 13 may be attached on the other surfaces of the carriage 3.

Furthermore, the embodiment described above has described the structure in which the sensor unit 13 includes the housing constituted by the base part 20 and the cover part 21. However, the housing included in the sensor unit 13 is not limited to that constituted by the base part 20 and the cover part 21. More specifically, the shape of the housing included in the sensor unit is not specifically limited to the shape shown in the embodiment described above as long as there is a space inside thereof for accommodating the sensor, and a hole and a light path opening are provided.

In addition, the embodiment described above has described the structure in which an air flows from the hole 40 in the shape shown as the ventilation opening in the figure to the light path openings 24a and 24b. However, the shape of the ventilation opening is not limited to the shape of the hole 40 shown in the figure in the embodiment described above as long as it is possible to discharge the air from the light path openings 24a and 24b and hinder the air flow from the light path openings 24a and 24b into the sensor unit 13. For example, the shape may be a slit.

Furthermore, the embodiment described above has described the case of using the sensor including the light emitting element and the light receiving element as the optical element for obtaining information from the medium. However, the sensor including no light emitting element may be used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-263665, filed Dec. 20, 2013, which is hereby incorporated by reference wherein in its entirety.

What is claimed is:

1. A liquid ejection apparatus, comprising:
 a movable carriage including an ejection head mounted thereon for ejecting a liquid onto a medium; and
 a sensor unit accommodating an optical element, the sensor unit being attached to the carriage,
 wherein the sensor unit has a first opening and a second opening which is communicated with the first opening and forms a light path between the optical element and the medium, and
 wherein the sensor unit includes a first part and a second part, the first part accommodates the optical element, the second part accommodates at least a part of the first part, and the first opening is formed in a clearance between an outer surface of the first part and an inner surface of the second part.

2. The apparatus according to claim 1, wherein the carriage moves in a reciprocating manner in a forward direction and a backward direction, and the sensor unit is provided further to the rear of the mounting position of the ejection head with respect to one of the forward direction and the backward direction, and the first opening opens toward the mounting position of the ejection head.

3. The apparatus according to claim 1, wherein an interval between the sensor unit and the medium is substantially equal to an interval between an ejection opening of the ejection head and the medium, and wherein a size of the first opening is larger than a size of the second opening.

4. The apparatus according to claim 1, wherein the first opening is opened in a direction intersecting with a moving direction of the carriage.

5. The apparatus according to claim 1, wherein the first opening is opened in the same direction as an opening direction of the second opening.

6. A liquid ejection apparatus, comprising:
a movable carriage including an ejection head mounted thereon for ejecting a liquid onto a medium; and
a sensor unit accommodating an optical element, the sensor unit being attached to the carriage,
wherein the sensor unit has a first opening and a second opening which is communicated with the first opening and forms a light path between the optical element and the medium, and
wherein an interval between the sensor unit and the medium is substantially equal to an interval between an ejection opening of the ejection head and the medium.

7. The apparatus according to claim 6, wherein the first opening is located above the ejection opening of the ejection head.

8. A liquid ejection apparatus, comprising:
a movable carriage including an ejection head mounted thereon for ejecting a liquid onto a medium; and
a sensor unit accommodating an optical element, the sensor unit being attached to the carriage,
wherein the sensor unit has a first opening and a second opening which is communicated with the first opening and forms a light path between the optical element and the medium, and
wherein an opening end of the first opening is away from a surface of the carriage by 10 mm or more, the surface including the sensor unit attached thereon.

9. A liquid ejection apparatus, comprising:
a movable carriage including an ejection head mounted thereon for ejecting a liquid onto a medium; and
a sensor unit accommodating an optical element, the sensor unit being attached to the carriage,
wherein the sensor unit has a first opening and a second opening which is communicated with the first opening and forms a light path between the optical element and the medium, and
wherein an opening area of the first opening is larger than an opening area of the second opening.

10. A sensor unit, comprising:
an optical element; and
a housing accommodating the optical element,
wherein the housing has a light path opening forming a light path between the optical element and outside, and a ventilation opening opened in a direction intersecting with an opening direction of the light path opening and communicated with the light path opening.

11. The sensor unit according to claim 10, wherein the housing includes a first part for attaching the optical element thereto, and a second part for accommodating at least a part of the first part, and
the ventilation opening is formed in a clearance between an outer surface of the first part and an inner surface of the second part.

* * * * *